United States Patent [19]

Uzuki et al.

[11] 3,991,077

[45] Nov. 9, 1976

[54] METHOD OF RACEMIZING OPTICALLY ACTIVE N-ACYLAMINO ACIDS

[75] Inventors: Teruo Uzuki; Mayumi Takahashi, both of Kawasaki; Misa Noda, Tokyo; Yoshioki Komachiya, Yokohama; Hachiro Wakamatsu, Musashino, all of Japan

[73] Assignee: Ajinomoto Co., Inc., Tokyo, Japan

[22] Filed: Mar. 3, 1975

[21] Appl. No.: 554,673

Related U.S. Application Data

[63] Continuation-in-part of Ser. No. 403,912, Oct. 5, 1973, abandoned.

[30] Foreign Application Priority Data

Oct. 19, 1972 Japan.............................. 47-104607
Oct. 27, 1972 Japan.............................. 47-107772

[52] U.S. Cl. ................ 260/326.14 T; 260/239.3 R; 260/309; 260/326.8; 260/518 R; 260/518 A; 260/519; 260/534 R; 260/534 C; 260/534 E; 260/534 M; 260/534 G; 260/534 S

[51] Int. Cl.²............... C07D 209/20; C07C 101/20; C07C 101/77; C07C 101/08

[58] Field of Search........ 260/534 R, 534 E, 534 M, 260/534 G, 534 S, 534 C, 518 R, 518 A, 519, 309, 239.3 R, 326.8, 326.14 T

[56] References Cited
UNITED STATES PATENTS
3,458,568   7/1969   Ogasawara et al............. 260/534 R OTHER PUBLICATIONS
Kameda et al., "Chem. Abstracts," vol. 54 (1960), p. 20890f.
Greenstein et al., "Chemistry of the Amino Acids," vol. 3, (1961), pp. 1950–1951.

*Primary Examiner*—Joseph E. Evans
*Attorney, Agent, or Firm*—Hans Berman; Kurt Kelman

[57] ABSTRACT

Optically active amino acids N-acylated with carboxylic acids are readily racemized without decomposition at elevated temperature in inert organic solvents in which they are homogeneously soluble at the racemization temperature. When the deacylated amino acid is insoluble or only sparingly soluble in the solvent, the method permits a convenient work-up of the products of enzymatic deacylation of one enantiomorph of the N-acylamino acid in which the remaining enantiomorph is racemized for recycling to the deacylation step.

9 Claims, No Drawings

METHOD OF RACEMIZING OPTICALLY ACTIVE N-ACYLAMINO ACIDS

This application is a continuation-in-part of our copending application Ser. No. 403,912, filed on Oct. 5, 1973, and now abandoned.

This invention relates to the racemization of optically active compounds, and particularly to the racemization of optically active N-acylamino acids whose acyl group is derived from carboxylic acids.

When racemic amino acids are produced synthetically, and only one of the optically active enantiomorphs is wanted, it is common practice to resolve the synthetic product to recover the desired enantiomorph, to racemize the unwanted antipode, and to recycle the racemization product to the resolution step. Racemization methods widely employed now rely on melting of the optically active material either in a gaseous medium or in an inert liquid in which the material is insoluble.

These common methods of thermal racemization cannot avoid local overheating of the material when large charges are to be treated, and result in partial decomposition and discoloration of the desired compound. The problem is particularly serious with N-acyl derivatives of amino acids whose acyl groups are derived from carboxylic acids, and which are referred to hereinafter as "acylamino acids" for brevity, the term "acyl" being understood in its limited sense which excludes the radicals of sulfonic acids and the like.

It has now been found that optically active N-acylamino acids can be racemized quickly, completely, and without significant decomposition at elevated temperatures in the presence of organic solvents in which they are soluble at the racemization temperature. Such solvents include triesters of phosphoric acid with alkanols or haloalkanols having up to eight carbon atoms, phenol, halophenols, or lower-alkyl phenols. The di-lower-alkyl formamides and sulfoxides, and di-lower-alkyl ketones are also suitable solvents. The terms "lower alkyl" and their analogs are used in this specification and the appended claims to indicate radicals and compounds having one to four carbon atoms. The term "halo" stands for chloro, bromo, and iodo, although halogen derivatives other than the chlorine derivatives offer no advantageous and are not economically attractive at this time.

N-acyl derivatives of all optically active amino acids are capable of being racemized by the method of the invention. The amino acids whose N-acyl derivatives are successfully racemized include not only the naturally occurring α-amino acids in which the amino group is bound directly to an asymmetric carbon atom, but also others that are available by synthesis only. The N-acyl groups apparently have no influence on the racemization process, and the economically important compounds in which the acyl group is derived from the lower alkanoic acids and their halogen substitution products and from analogous aromatic acids are readily racemized. Typical acyl groups thus include the formyl, acetyl, propionyl, chloroacetyl, benzoyl, and chlorobenzoyl groups.

The phosphoric acid esters successfully employed as solvents in the racemization method of the invention include the triesters of phosphoric acid with methanol, ethanol, chloroethanol, N-propanol, isopropanol, n-butanol, isobutanol, tert-butanol, pentanol, octanol, phenol, chlorophenol, cresol. The three alcohol moieties in the phosphoric acid triester need not be the same. Mono-octyl-diphenyl phosphate and methyl-propyl-butyl phosphate are as effective as esters having three identical alcohol moieties since no chemical reaction is involved.

The di-lower-alkyl-formamides conveniently available at reasonable cost are dimethylformamide, methylethylformamide, and diethylformamide, and are preferred in the absence of significant advantages to be obtained or to be expected from the higher homologs.

While acetone is operative in the method of the invention, its vapor pressure is too high at the temperatures at which the racemization proceeds at adequate speed to make it economically attractive. Methylethylketone has been used successfully in readily available equipment, and diethylketone and higher homologs, as far as conveniently available and readily processed, are similarly effective.

Dimethylsulfoxide and diethylsulfoxide are the only di-lower-alkyl-sulfoxides presently available to us in commercial quantities, as are the corresponding formamides.

The phosphoric acid esters are preferred over other solvents in many instances because of their low vapor pressures at the temperatures at which the racemization of N-acylamino acids proceeds at a high rate, permitting the racemization to be carried out in vessels open to the atmosphere and without need for reflux condensers. The esters of alcohols having up to five carbon atoms and of their halogen derivatives are most readily separated from the racemization products.

The temperature at which the racemization is performed may be chosen more freely in the method of the invention than in the known methods of thermal racemization to suit the properties of the material to be racemized and the desired quality of the product. Temperatures between 90° and 200° C are generally applicable without significant decomposition or discoloration of the material processed.

The ratio of the optically active material and the solvent in the racemization mixture has a decisive influence on the rate at which the racemization proceeds under otherwise identical conditions. A reduction of the racemization rate with increasing solvent content of the mixture is observed generally for all N-acylamino acids and for all solvents of this invention. The weight of the solvent should not exceed seven times the weight of the N-acylamino acid to be racemized, and an upper limit of five parts solvent per part of optically active N-acylamino acid is preferred. However, the amount of solvent employed must be sufficient to dissolve the entire N-acylamino acid at the racemization temperature chosen. It is not necessary that the N-acylamino acid be soluble in the available solvent at lower temperatures. For operation on an industrial scale, the amount of solvent should be at least 0.5 part by weight per part of N-acylamino acid to avoid local overheating, and equal parts of solvent and N-acylamino acid are generally safer.

The following Table shows the percentage of N-acetyl derivatives of various L-amino acids racemized when held at 180° C for 30 minutes in mixtures with tri-n-butyl phosphate at respective weight ratios of 1:2 and 1:20.

TABLE

| L-Amino acid | Racemization Rate, % | |
|---|---|---|
| | 1:2 | 1:20 |
| Phenylalanine | 100 | 22.0 |
| Methionine | 93.9 | 33.5 |
| Leucine | 99.1 | 20.4 |
| Valine | 94.1 | 5.1 |
| Aspartic Acid | 68.2 | 32.3 |
| Tryptophan | 94.6 | 21.7 |
| Alanine | 63.5 | 3.7 |

The racemic N-acylamino acid may be recovered from the racemization mixture by methods conventional in themselves. When the solvent employed is insoluble or only sparingly soluble in water, the product may be extracted from the mixture with water, and crystallized from the aqueous extract. When the solvent is readily soluble in water, the diluted mixture may be adjusted to the isoelectric point of the N-acylamino-DL-acid to induce crystallization of the latter. The solvent, if volatile at sufficiently low temperature, may be removed from the mixture, and other methods of recovery will be exemplified below and will be obvious to those skilled in the art.

The racemization method of this invention has been found to be particularly advantageous when applied to the mixture of L-amino acid and N-acyl-D-amino acid which results from the action of acylase on an N-acyl-DL-amino acid in an aqueous medium. The optically active amino acid having an unsubstituted amino group is not readily soluble in the solvents of the invention, so that the products of partial hydrolysis caused by the acylase may be extracted with solvents of the invention to separate the optically active N-acylamino acid from the oppositely active amino acid, and the solution of the N-acylamino acid may then be heated to racemize the product and make it ready for further attack by acylase. This permits an N-acyl-DL-amino acid to be converted in its entirety into one optically active enantiomorph of the unsubstituted amino acid.

The deacylation mixture produced by the acylase may first be stripped of its water content, and the solid residue may be fractionated by extraction with a solvent of the invention, and this procedure is preferred when the solvent employed is soluble in water. If the optically active N-acylamino acid is present in the deacylation mixture as a salt, the mixture or its residue must be acidified prior to extraction because the salts of N-acylamino acids are not soluble in the solvents of this invention. The solubility of solvents of this invention in water may be decreased by the simultaneous presence of sodium or potassium chloride.

If the extract of the optically active N-acylamino acid produced in the manner described above contains more solvent than is desirable for the racemization step, the excess may be removed by evaporation, preferably in a vacuum.

The following Examples are further illustrative of this invention.

EXAMPLE 1

Mixtures of 2 g N-acetyl-L-phenylalanine and 1 g tri-n-butyl phosphate were held at 160°, 170°, and 180° C respectively, and the optical rotation of the mixtures, which rapidly became homogeneous at the temperatures chosen, was monitored. Complete racemization occurred at 160° C within 25 minutes, at 170° C within 15 minutes, and at 180° C within 10 minutes.

When N-acetyl-L-phenylalanine was held at the same temperatures in the absence of the solvent, only 81.4% of the compound was racemized after 150 minutes at 150° C, 91.1% after 20 minutes at 170° C, and racemization was complete only after 10 minutes at 180° C, the melting point of the compound being 172° C.

When N-acetyl-L-phenylalanine was dispersed in twice its weight of refined paraffin oil (Nujol) in which it is insoluble, and the mixture was held at 180° C for 60 minutes, the amino acid was completely racemized, but decomposed enough to make the mixture dark and opaque. Recovery of pure N-acetyl-DL-phenylalanine was difficult.

EXAMPLE 2

A mixture of 5 g N-acetyl-L-phenylalanine crystals and 20 g tri-n-butyl phosphate was heated with stirring for 30 minutes in an open 50 ml vessel immersed in an oil bath at 180° C. The crystals disappeared within about 1 to 2 minutes, and a homogeneous solution was formed. The vessel therafter was plunged in cold water to cool its contents, and the reaction mixture was diluted to 100 ml with tri-n-butyl phosphate.

It showed no optical rotation, and the racemization thus was complete.

The diluted solution was extracted with 50 ml aqueous 3% sodium hydroxide solution, and the extract was adjusted to pH 1.0 with concentrated sulfuric acid with stirring and cooling. The N-acetyl-DL-phenylalanine precipitated thereby in crystalline form was recovered. It weighed 4.57 g (91.3% yield) and melted at 150° – 151° C.

EXAMPLE 3

A mixture of 5 g N-acetyl-L-leucine and 10 g tri-n-butyl phosphate was heated 30 minutes at 180° C as in Example 2, quickly cooled, diluted to 100 ml with tri-n-butyl triphosphate, and tested for its optical rotation. A specific rotatory power of $[\alpha]_D^{25} = -0.15°$ was found, indicating 99.1% racemization.

N-Acetyl-DL-leucine was extracted from the racemization mixture with 3% sodium hydroxide and precipitated in crystalline form when the extract was adjusted to pH 1.0. The crystals weighed 4.66 g, melted at 155° C, and did not show measurable rotatory power.

EXAMPLE 4

5 g Crystalline N-acetyl-L-aspartic acid and 7 g tri-n-butyl phosphate were heated in a 50 ml vessel to 180° C with stirring for 50 minutes, and the chilled racemization mixture was diluted to 100 ml with tri-n-butyl phosphate. It showed a specific rotation of $[\alpha]_D^{25} = -0.67°$ indicating a racemization rate of 96.4%.

EXAMPLE 5

A mixture of 50 g crystalline N-acetyl-L-methionine and 100 g tri-n-butyl phosphate was stirred in a 300 ml flask for 30 minutes while the open flask was immersed in an oil bath at 180° C. The mixture thereafter was cooled quickly and extracted with 200 ml of an aqueous solution containing 10.5 g sodium hydroxide. The extract was partly evaporated to 100 ml, and the concentrate was adjusted to pH 1 with sulfuric acid as in Example 2. The precipitated cyrstalline product was pure, optically inactive N-acetyl-DL-methionine weighing 35.6 g and melting at 114° C.

EXAMPLE 6

5 g Crystalline N-acetyl-L-phenylalanine and 10 g triethyl phosphate were heated in a 50 ml vessel for 60 minutes at 180° C and ambient pressure. The crystals dissolved at an early stage of the heating process. The racemization mixture was quickly cooled by immersing the vessel in cold water, diluted with triethyl phosphate to 100 ml, and tested for optical rotation. None was found.

EXAMPLE 7

A mixture of 5 g N-acetyl-L-valine and 10 g tri-2-chloroethyl phosphate was heated for 30 minutes at 180° C in a 50 ml vessel as in Example 2, chilled, and diluted to 100 ml with tri-2-chloroethyl phosphate. The diluted solution showed no optical activity, indicating 100% racemization.

Crystalline N-acetyl-DL-valine melting at 146° C and weighing 4.31 g was recovered by extraction with dilute sodium hydroxide solution and acidification of the extract, as described above.

EXAMPLE 8

5 g N-formyl-L-3,4-dimethoxyphenylalanine and 10 g tri-n-butyl phosphate were stirred at 180° C and atmospheric pressure for 30 minutes in a 50 ml vessel. The racemization mixture was then cooled, diluted to 100 ml with tri-n-butyl phosphate, and tested for optical activity. None was found.

It was then extracted with 50 ml 3% sodium hydroxide solution, and 2.9 g crystalline N-formyl-DL-3,4-dimethoxyphenylalanine melting at 134° C was recovered from the acidified extract as described in the preceding Examples in more detail.

EXAMPLE 9

N-Benzoyl-L-leucine was converted to crystalline N-benzoyl-DL-leucine by the procedure of Example 9 in a yield of 91.4%. It melted at 138° C and lacked measurable optical activity.

EXAMPLE 10

5 g Crystalline N-acetyl-L-leucine and 10 g dimethyl sulfoxide in an open 50 ml vessel were heated 60 minutes at 180° C with stirring. The racemization mixture was then chilled quickly by immersing the vessel in cold water, and the solution was diluted to 100 ml with dimethyl sulfoxide for a test of its optical rotation which was found to be $[\alpha]_D^{25} = -0.43°$, indicating a racemization rate of 98.19%.

EXAMPLE 11

5 g Crystalline N-acetyl-L-phenylalanine and 5 g dimethylformamide were placed in a 50 ml reaction vessel equipped with a reflux condenser which was then immersed in an oil bath at 160° C. The mixture was permitted to reflux for three hours, and was then cooled quickly. It was diluted to 100 ml with dimethylformamide, and its optical rotation was then found to be $[\alpha]_D^{25} = +0.17°$, corresponding to 96.40% racemization of the N-acetyl-L-phenylalanine.

EXAMPLE 12

31.7 g (0.153 Mole) N-acetyl-DL-phenylalanine and 6.12 g (0.153 mole) sodium hydroxide were dissolved in 300 ml water, and the solution was adjusted to pH 7.0. 0.02 g Crystalline cobaltous chloride hexahydrate and 1.59 g acylase (19,000 units/g) were added, and the mixture was stirred 10 hours at 37° C, whereby the N-acetyl-D-phenylalanine was not affected, while the antipode present, 90.1% of the N-acetyl-L-phenylalanine, was hydrolyzed by the enzyme to L-phenylalanine.

When the reaction mixture was partly evaporated to 40 ml, the L-phenylalanine crystallized while the N-acetyl-D-phenylalanine and residual N-acetyl-DL-phenylalanine remained in the solution as the sodium salts. The L-phenylalanine was filtered off, washed with 10 ml water, and dried. It weighed 9.58 g (0.058 mole).

The mother liquor was adjusted to pH 1.0 with concentrated hydrochloric acid in a separating funnel, whereby crystalline N-acetyl phenylalanine was precipitated, and 300 ml tri-n-butyl phosphate was added. The resulting mixture was agitated for 30 minutes at ambient temperature and then permitted to settle. The aqueous layer was separated, evaporated to a volume of 50 ml, and adjusted to pH 5.0, whereby 1.15 g crude L-phenylalanine was crystallized, increasing the yield of crude L-phenylalanine to 10.73 g (94.3%).

The tri-n-butyl phosphate phase containing N-acetyl-D-phenylalanine was evaporated to about 30 ml at less than 170° C in a vacuum, and was then heated at 180° C for 30 minutes at ambient pressure, whereby all optical activity disappeared. The N-acetyl-DL-phenylalanine recovered from the concentrate as described in preceding Examples was added to another batch of the racemic compound before the latter was subjected to acylase treatment in a new, identical cycle.

EXAMPLE 13

64.8 g (0.339 Mole) N-acetyl-DL-methionine crystals and 13.6 g (0.339 mole) sodium hydroxide were dissolved in 600 ml water, and the solution was adjusted to pH 8.0. 0.02 g Cobaltous chloride hexahydrate and 3.24 g acylase (19,000 units/g) were added, and the mixture was stirred 24 hours at 38° C to convert 92.3% of the N-acetyl-L-methionine present to the corresponding methionine enantiomorph.

The solution was then adjusted to pH 2.0 with sulfuric acid and agitated for 30 minutes at room temperature with 500 ml tri-n-butyl phosphate. The aqueous phase was separated and agitated with a second batch of 500 ml tri-n-butyl phosphate.

The extracted aqueous liquid was partly evaporated to 100 ml and adjusted to pH 5.5, whereby L-methionine crystals were precipitated. They were recovered and weighed 19.64 g (84.1% yield). The combined tri-n-butyl phosphate phases were washed with 500 ml water, and an aliquot was subjected to gas chromatography which indicated the presence of 92% of the remaining N-acetylmethionine.

The bulk of the tri-n-butyl phosphate solution was evaporated in a vacuum to 100 ml and then heated 30 minutes at 180° C. The specific rotatory power of the solution then was $[\alpha]_D^{25} = -0.08$, indicating practically complete racemization of the N-acetyl-D-methionine originally present which, under the same conditions, would have produced a specific rotation of −8.54°.

EXAMPLE 14

N-Acetyl-DL-leucine was selectively hydrolyzed by means of acylase at pH 7.0, and 100 ml of the hydrolysis mixture contained 5.0 g N-acetyl-D-leucine, 3.79 g L-leucine, and 1.21 g sodium acetate. The solution was adjusted to pH 1.0 with concentrated sulfuric acid in a separating funnel, whereby crystalline n-acetyl-d-leucine precipitated. The mother liquor was evaporated to dryness, and the residue together with the precipitated N-acetyl-D-leucine was stirred with 100 ml dimethyl sulfoxide which dissolved all the N-acetyl-D-leucine present. The solution was evaporated in a vacuum to 30 ml, and then heated 60 minutes at atmospheric pressure to 180° C. It no longer showed any rotatory power.

The residue insoluble in dimethyl sulfoxide was dissolved in 30 ml water and the solution was adjusted to pH 5.5 whereby L-leucine was crystallized in an amount of 3.46 g (91.3% yield).

EXAMPLE 15

A hydrolyzation mixture prepared from N-acetyl-DL-tryptophan by interaction with acylase in the manner of the preceding Examples had a volume of 200 ml, and contained 5.0 g N-acetyl-D-tryptophan, 4.15 g L-tryptophan, and 0.85 g sodium acetate. It was adjusted to pH 0.5 with concentrated sulfuric acid, whereby crystalline N-acetyl-D-tryptophan was precipitated, but was not separated from the mother liquor. 100 ml Tri-n-butyl phosphate was added, and the mixture was agitated at room temperature for 30 minutes. The two phases were permitted to separate, and the aqueous phase was again extracted with 100 ml tri-n-butyl phosphate at room temperature by 30 minutes' agitation.

The aqeuous liquid was then adjusted to pH 5.5 with sodium hydroxide to precipitate L-tryptophan which weighed 2.85 g (68.7% yield). −

The combined organic solutions were evaporated in a vacuum to 18 ml, and the concentrate was heated at 180° C for 30 minutes. Its specific rotatory power $[\alpha]_D^{25}$ was 31 0.21°, indicating almost complete racemization of the N-acetyl-D-tryptophan.

EXAMPLE 16

A solution of 31.7 g N-acetyl-DL-phenylalanine and 6.12 g sodium hydroxide in 300 ml water was adjusted to pH 7.0, mixed with 0.02 g cobaltous chloride hexahydrate, and 1.59 g acylase, and stirred 24 hours at 37° C whereby 98.3% of the available L-phenylalanine was formed, as determined by paper chromatography.

The reaction solution was evaporated to 40 ml, and L-phenylalanine was crystallized. The crystals recovered by filtering, washed with 10 ml distilled water, and dried weighed 10.6 g (93.1% yield).

The combined mother liquor and washings (50 ml) were adjusted to pH 1.0 with concentrated hydrochloric acid, 300 ml triethylphosphate and 10 g sodium chloride were added, and the mixture was agitated at room temperature for 30 minutes. The organic phase was separated, evaporated to 50 ml, and heated 1 hour at 180° C. It was free from optical activity, indicating that the N-acetyl-D-phenylalanine had been completely racemized.

EXAMPLE 17

100 ml Acylase reaction solution containing 6.11 g N-acetyl-D-valine, 0.95 g L-valine, and 3.15 g sodium acetate was adjusted to pH 1.0 with concentrated sulfuric acid, and 300 ml methylethylketone and 20 g sodium chloride were added. The mixture was agitated 30 minutes at room temperature. The ketone phase was separated from the aqueous phase and contained 4.56 g N-acetyl-D-valine, as determined by acid titration, or 91.1% of the entire N-acetyl-D-valine present. It was evaporated to about 15 ml, and the concentrate was heated 1 hour at 160° C in a closed vessel. No optical activity could be detected in the solution after it was cooled to room temperature, indicating complete racemization of the N-acetyl-D-valine.

Analogous results were achieved with the optically active N-acyl derivatives of alanine, isoleucine, norleucine, serine, threonine, glutamic acid, cystine, cysteine, p-chlorophenylalanine, tyrosine, phenylglycine, DOPA, 3,4-methylene-dihydroxyphenylalanine, proline, hydroxyproline, 5-hydroxytryptophan, histidine, α-amino-ε-caprolactam, lysine, ornithine, and arginine. Both the mono-acyl and the N,N'-diacyl derivatives of the last-mentioned basic amino acids could be racemized, but the formation of by-products could not be entirely suppressed during racemization of the monoacyl derivatives.

What is claimed is:

1. A method of thermally racemizing an optically active enantiomorph of an N-acylamino acid which comprises:
   a. mixing said enantiomorph with a solvent selected from the group consisting of
      1. a triester of phosphoric acid with an alkanol or haloalkanol having up to eight carbon atoms, phenol, halophenol, or lower-alkyl-phenol,
      2. a di-lower-alkylformamide,
      3. a di-lower-alkylsulfoxide, and
      4. a di-lower-alkylketone; and
   b. holding the resulting mixture at a temperature between 90° and 200° C until said enantiomorph is substantially completely racemized to the corresponding N-acyl-DL-amino-acid,
      1. the acyl of said N-acylamino acid being lower alkanoyl, halo-lower-alkanoyl, benzoyl, or halobenzoyl,
      2. said lower alkanoyl and lower alkyl having one to four carbon atoms,
      3. said halo being chloro, bromo, or iodo,
      4. the weight of said solvent in said mixture being sufficient homogeneously to dissolve said enantiomorph at said temperature, but not greater than seven times the weight of said enantiomorph.

2. A method as set forth in claim 1, wherein said enantiomorph is an N-acyl derivative of phenylalanine, aspartic acid, methionine, valine, dimethoxyphenylalanine, leucine, or tryptophan.

3. A method as set forth in claim 2, wherein said acyl is acetyl, formyl, or benzoyl.

4. A method as set forth in claim 3, wherein said solvent is triethyl phosphate, tributyl phosphate, tri-2-chloroethyl phosphate, dimethylsulfoxide, dimethylformamide, or methylethylketone.

5. A method as set forth in claim 1, wherein said enantiomorph prior to said mixing is produced by exposing the optically inactive form of said N-acylamino acid to acylase in an aqueous medium until the antipode of said enantiomorph is converted to the corresponding optically active amino acid.

6. A method as set forth in claim 5, wherein the interaction of said acylase with said inactive form results in an aqueous solution of said enantiomorph and of said optically active amino acid, said solvent is not more than sparingly soluble in water, and said mixing includes extracting said aqueous solution with said solvent while said aqueous solution is acidic.

7. A method as set forth in claim 5, wherein the interaction of said acylase with said inactive form results in an aqueous solution of said enantiomorph and of said optically active amino acid, the water is removed from said solution having an optically active free N-acyl amino acid, and said mixing includes extracting the resulting residue with said solvent.

8. A method as set forth in claim 1, wherein said resulting mixture consists essentially of said enantiomorph and of said solvent.

9. A method as set forth in claim 8, wherein the N-acylamino group of said enantiomorph is bound directly to an asymmetric carbon atom.

* * * * *